US011962053B2

(12) United States Patent
Krumme et al.

(10) Patent No.: US 11,962,053 B2
(45) Date of Patent: Apr. 16, 2024

(54) ROTARY JOINT WITH DIELECTRIC WAVEGUIDE

(71) Applicant: Schleifring GmbH, Fürstenfeldbruck (DE)

(72) Inventors: Nils Krumme, Feldafing (DE); Holger Steffens, Munich (DE)

(73) Assignee: SCHLEIFRING GMBH, Fürstenfeldbruck (DE)

( * ) Notice: Subject to any disclaimer, the term of this patent is extended or adjusted under 35 U.S.C. 154(b) by 881 days.

(21) Appl. No.: 16/991,506

(22) Filed: Aug. 12, 2020

(65) Prior Publication Data

US 2020/0373641 A1  Nov. 26, 2020

Related U.S. Application Data

(63) Continuation of application No. PCT/EP2019/057262, filed on Mar. 22, 2019.

(30) Foreign Application Priority Data

Mar. 22, 2018 (EP) ..................... 18163449

(51) Int. Cl.
*H01P 1/06* (2006.01)
*H01P 3/16* (2006.01)
*H04B 3/52* (2006.01)

(52) U.S. Cl.
CPC ............. *H01P 1/068* (2013.01); *H01P 3/16* (2013.01); *H04B 3/52* (2013.01)

(58) Field of Classification Search
CPC . H01P 1/068; H01P 3/16; A61B 6/032; A61B 6/56; H04B 3/52; H04B 5/0012; H04B 5/0018; G02B 6/3604
See application file for complete search history.

(56) References Cited

U.S. PATENT DOCUMENTS

| 4,692,721 A * | 9/1987 | Ito ........................ H01P 1/068 |
| | | 333/261 |
| 4,800,350 A | 1/1989 | Bridges |
| 5,530,422 A | 6/1996 | Harrison |
| 5,600,697 A | 2/1997 | Harrison |

(Continued)

FOREIGN PATENT DOCUMENTS

| CN | 101036583 A | 9/2007 |
| CN | 104467924 A | 3/2015 |

(Continued)

OTHER PUBLICATIONS

International Searching Authority, International Search Report and Written Opinion for PCT/EP2019/057262, dated May 28, 2019.

(Continued)

*Primary Examiner* — Andrea Lindgren Baltzell
*Assistant Examiner* — Kimberly E Glenn
(74) *Attorney, Agent, or Firm* — Quarles & Brady LLP; Yakov S. Sidorin (57) ABSTRACT

A contactless datalink for transmission of data between a rotatable part and a stationary part, including a dielectric waveguide split into two sections. A first dielectric waveguide section is at the rotatable part and a second dielectric waveguide section is at the stationary part. The first dielectric waveguide section is coupled to a transmitter and the second dielectric waveguide section is coupled to a receiver.

14 Claims, 8 Drawing Sheets

(56) References Cited

U.S. PATENT DOCUMENTS

| | | |
|---|---|---|
| 9,871,283 B2 | 1/2018 | Henry |
| 2007/0063785 A1 | 3/2007 | Krumme |
| 2008/0036558 A1 | 2/2008 | Suarez-Gartner |
| 2017/0332991 A1 | 11/2017 | Fackelmeier |

FOREIGN PATENT DOCUMENTS

| | | |
|---|---|---|
| CN | 111200373 A | 5/2020 |
| DE | 3538035 A1 | 4/1987 |
| DE | 102015105657 A1 | 12/2018 |
| EP | 1729646 B1 | 12/2006 |
| EP | 2932901 A1 | 10/2015 |
| EP | 3203287 A1 | 8/2017 |
| EP | 3309898 A1 | 4/2018 |

OTHER PUBLICATIONS

Shankang, L. Recent Progress in Spiral Scan Mode of X-CT Unit. CT Theory and Applications. vol. 1, No. 2. May 1992. Includes English Abstract on p. 5.

\* cited by examiner

ROTARY JOINT WITH DIELECTRIC WAVEGUIDE

CROSS-REFERENCE TO RELATED APPLICATIONS

This application is a continuation of the pending International Application No. PCT/EP2019/057262 filed on 22 Mar. 2019, which designates the United States and claims priority from European Application No. 18163449.4 filed on 22 Mar. 2018. The disclosure of each of the above-identified patent applications is incorporated herein by reference.

BACKGROUND

1. Field of the Invention

The invention relates to high speed datalinks for non-contacting or contactless signal and data transmission, in particular to rotating transmission devices such as rotary joints. Such transmission devices may be used in computer tomography scanners, also called CT scanners. These datalinks may be used in a mm-wave range.

2. Description of Relevant Art

Contactless rotatable couplers, also called contactless rotary joints, are used to couple signals and data between parts rotatable against each other. For example, in CT scanners, a rotating x-ray tube and an x-ray detector generate high-speed imaging data. The data may be transmitted from the rotating part to the stationary part. Furthermore, control signals for controlling the device and, specifically, the power supply of the x-ray tube may be transmitted from the stationary to the rotating part and vice versa. Many further applications exist, where there is the need to transmit control signals or data between a rotor and a stator—for example in windmills, revolving transfer machines, bottling plants, packaging machines or placement heads of insertion machines.

A capacitive rotary joint for CT scanners is disclosed in U.S. Pat. No. 5,600,697. A large diameter rotating ring carries a differentially driven strip line guiding a signal along this circumference of the ring. The strip line has copper conductors on a PCB base. This strip line has a bandwidth limited to a few GHz and therefore a data rate limited to a few Gbit/s.

A dielectric cable is disclosed in US 2008/036558 A1. A hybrid plastic waveguide is disclosed in EP 3203287 A1. A dielectric waveguide using powdered material is disclosed in US 448004350. A tiltable waveguide member using a ball and socket configuration is disclosed in U.S. Pat. No. 9,871,283 B1. DE 102015105657 A1 discloses a connector for dielectric waveguides.

EP1729646 discloses a datalink based on a dielectric waveguide. The couplers for coupling signals into and out of the waveguide are comparatively complex. EP 3309898 A1 discloses an antenna module for millimeter-wave communication which combines transmit and receive signals to a transceiver and couples them into a dielectric waveguide by an antenna.

SUMMARY

The embodiments are providing a contactless datalink for transmission of data between rotating parts in a millimeter waveband. The device may be simple, easy to install, easy to maintain and cost-efficient.

In an embodiment, a contactless datalink configured to transmit data between a rotatable part and a stationary part includes a ring-shaped dielectric waveguide that is split into two components, preferably two identical and/or symmetrical components and forming a disc configuration. One component, for example a first component, may be mounted at the stationary part of a device, and a second component may be mounted at the rotatable part. The dielectric waveguide may have a round cross section, or an oval cross-section, or a rectangular cross section. In an embodiment, the rotatable and stationary parts may be exchanged (in that a rotatable part can be configured to be stationary, while a stationary part can be configured to be rotatable). Preferably, there is a gap between the two components in a plane that is transverse—and preferably orthogonal—to the rotation axis, which axis forms the center of rotation. In another embodiment, the ring may be split cylindrically and parallel to the rotation axis to form a drum configuration. Any configuration allows coupling of signals from either side to the other side. The ring-shaped dielectric waveguide preferably has a center axis substantially aligned with the axis of rotation between the rotatable and the stationary part. Here the term of identical and/or symmetrical components preferably relates to the structure of these components, for example cross section or ring diameter. They may include different sections as disclosed herein.

The width of the gap is preferably dimensioned in the range of $1/10$th to $1/8$th of a wavelength (of a signal transmitted through the dielectric waveguide) in air and may have any size between nearly zero and $1/4$th of a wavelength in air. There may be changes and variations in this dimensional range—for example, caused by mechanical tolerances. Later, reference will be made to these waveguide components as waveguides.

The dielectric waveguide may have a cladding including a dielectric with lower dielectric constant than that of the core. The core of the dielectric waveguide may have a round cross-section, or an oval cross-section, or a rectangular crosssssection.

The split waveguide preferably is held by a mechanical support or cladding that has a lower dielectric constant than that of the waveguide itself, and which mechanical support may include, for example, a plastic foam or a different material.

The waveguide preferably has a low dielectric constant and low losses in the frequency range at and above 60 GHz (Millimeter-Wave range, which is defined as having a wavelength between 1 mm and 10 mm, which corresponds to a frequency range of 30 GHz to 300 GHz. This frequency band is called EHF or Extremely High Frequency band). Preferred materials are plastics with a low relative dielectric constant (1.5 to 3.5) and low losses, for example Polytetrafluorethylene (PTFE) and (PP) Polypropylene, Polyethylene or Polystyrene, chlorinated Polyethylene (CPE), Polyether ether ketone (PEEK), Polyphenylene sulfide (PPS), Cyclo-olefin polymer (COP) or Polyimide or combinations thereof. In one embodiment, the waveguide is made from solid plastic. It may also be filled with ceramics or made as foam to adjust the dielectric constant.

In one embodiment, which may be based on a waveguide structure as described above, a stationary waveguide (or a waveguide component) forming a circle with two waveguide sections, preferably both located in a plane transverse to the axis of rotation, and around the axis of rotation, is split in two sections that preferably have the same length. A second waveguide component at the second part—which may be the rotatable part of the device—includes also a first section and a second section. Preferably, such second, rotatable waveguide component is substantially symmetrical with respect to the first waveguide component, and mounted close to the first waveguide component to form a narrow gap therebetween. The stationary waveguide component and the rotatable waveguide component are in close proximity with each other such that signals are coupled between the stationary and rotatable waveguides, preferably in both directions—from the stationary waveguide component to the rotatable waveguide component and from the rotatable waveguide component to the stationary waveguide component. Preferably all waveguide sections have approximately equal lengths, and therefore each waveguide section—whether a waveguide section of the first, stationary waveguide or a wavesection of the second, rotatable waveguide—covers about half the circumference of their part, corresponding to an angle of approximately 180 degrees. The first stationary waveguide section and the second stationary waveguide section are connected with their two ends (that are located close together) to a 3 dB coupler, which is further coupled to a receiver. The 3 dB coupler combines the signals from both stationary waveguide sections and forwards these to the receiver. At the opposing ends of the first stationary waveguide section and the second stationary waveguide section, there may be coupled the absorbers. Similarly, the rotatable waveguide sections are connected with their ends (that are located close together) to a corresponding 3 dB coupler, which is further connected to a transmitter. The signals from the transmitter are forwarded to the 3 dB coupler, which splits a given signal into two equal signals that are then fed into the corresponding rotatable waveguide sections. The opposing ends of the rotatable waveguide sections may also be terminated by respective absorbers.

In a related embodiment, the stationary waveguide sections are connected at positions close to each other with a transmitter and a receiver, such that the first stationary waveguide section is connected to receiver, and the second stationary waveguide section is connected to a transmitter. The first rotatable section is connected at a first end with a first 3 dB coupler, which is further connected to a receiver. The second end is connected to a second 3 dB coupler which is further connected to a transmitter. Further, as viewed in a clockwise direction around the waveguide structure, the first end of the second rotatable waveguide section is connected to the first 3 dB coupler, whereas the second end of the second rotatable waveguide is connected to the second 3 dB coupler. This configuration allows for signal transmission without change in phase. The angular gap prevents cross-coupling. The term of "close to" may refer to the ends of dielectric waveguide sections that are in proximity to each other.

In a further embodiment, several substantially identical or different of the above described embodiments might be installed in parallel or antiparallel to increase the data transmission capacity in a given application.

In yet another embodiment, the dielectric waveguide is configured as a closed loop. Such loop may have a circular shape and be configured as one, single unitary part, or have an alternative structure in which both ends are glued or welded together. This circular dielectric waveguide might be fixed to the stator (thus becoming a stationary waveguide) or to the rotor (and be a rotatable waveguide). The cross-section of the waveguide may be circular, elliptic, oval, or rectangular, or have any other shape appropriately suited to guide a chosen wave. In an embodiment, this waveguide may be substantially identical to one waveguide section as described above. Whether the waveguide includes a single section of is split into two sections extended along one another, each of the sections that are present is configured to guide a wave and/or the two sections "split" from one another are configured to guide a given wave together, jointly.

There may be at least two couplers configures as sections of dielectric waveguides as described herein. These couplers may be used to couple a wave in and/or out of the closed-loop waveguide. These couplers generally are kept in close distance to one another, preferably dimensioned to have a physical length in the range of $\frac{1}{6}^{th}$ to $\frac{1}{10}^{th}$ of a wavelength in air, the distance may be in a range between near zero and up to $\frac{1}{4}^{th}$ of a wavelength (because of mechanical tolerances). The couplers preferably are mounted as circular segments having the same center point as that of the closed loop waveguide. The lengths of the two couplers preferably are substantially identical and are shorter than half of the total circumference of the closed loop.

The closed-loop waveguide may also be configured to rotate at a different speed than that of the rotatable coupler. Since depending on the specific of a given configuration the closed-loop waveguide can be made either rotatable or stationary, one of the couplers may be mounted in a fixed position and at a fixed distance to the closed-loop waveguide. The rotatable coupler may be mounted in such a way that it cannot collide with the stationary coupler during the rotation (in other words, mounting configuration for the rotatable coupler prevents the collision between the rotatable copler and the stationary coupler during the operation of the device). This means that one of the two couplers (e.g. the stationary coupler) may be mounted on the inner side of the waveguide, while the other coupler (e.g. the rotatable coupler)—on the outer side. Alternatively, the couplers may be mounted in front of or behind the closed-loop waveguide or at any angular position where a collision between them is avoided.

The stationary couplers may have the same lengths and/or the rotatable couplers may have the same lengths. Additionally or in the alternative, the stationary couplers may have the same lengths as those of the rotatable couplers.

One or both of the couplers may also be part of a waveguide section as described above. That means that the coupler is formed of a part of the other section of a waveguide that is split into two sections, where either of the section can guide a wave but also the combination of the two sections is configured to guide the wave. Preferably, this is the rotatable coupler when the closed loop waveguide is stationary.

The transceivers of the embodiments may include a transmitter and receiver that are connected to one port of the transceiver for wireless transmission and reception of the signals. This port can also be used for "wired" communication through a dielectric waveguide, if the port is coupled to a dielectric waveguide configured to guide the wave of choice. The stationary transceiver has one port to transmit and receive signals wirelessly and is connected to the stationary coupler either by a connecting dielectric waveguide or by directly coupling a wave into the coupler e.g. by an antenna. Just as the stationary transceiver, the rotatable transceiver may also have one port to transmit and receive signals wirelessly, and is connected to the stationary coupler. The waveguide and couplers (which are also formed of waveguide elements as described) are in close contact which each other such that signals are coupled between the stationary and rotatable coupler with the waveguide in between, and preferably in both coupling directions.

In one example, data transmitted up (from the stationary transceiver to the rotary or rotational transceiver) are propagating as waves in the waveguide in a clockwise direction, the data transmitted down (from the rotary transceiver to the stationary transceiver) are propagating in the contrary direction. Preferably, the closed-loop waveguide has an attenuation low enough to allow communication between the both transceivers during a first round of the waves travelling but high enough not to distort the receiver after the first round is completed.

Pairs of couplers may be connected to the transceivers either at ends that are close to each other or at ends that are distant and separated by the length of the couplers.

In another embodiment with transceivers offering more than one RF (Radio Frequency) port, multiple parallel communications can be increased by employing more than one closed-loop waveguide with rotatable and stationary couplers that are connected to the ports of one or more transceivers.

Preferably, the stationary transceiver generates and modulates RF (Radio Frequency) signals in the range of and above 60 GHz and couples a wave into the dielectric waveguide, where it propagates towards the stationary transceiver and vice versa. The technology can also be used with waves at substantially all carrier frequencies that can be coupled into dielectric waveguides, e.g. operating at 2.4 GHz or 5 GHz or any frequency above that (but below optical frequencies).

Preferably, the transceivers are employing the MIMO (multiple in-multiple out) technology as e.g. defined in recent substandards of IEEE-802.11-(WiFi/WLAN-Standard) e.g. IEEE-802.11n—and newer substandards-(WiFi/WLAN-Standard). Another implementation is configured according to a widely used commercial standard such as LTE, at e.g. 2.6 GHz. These standards for wireless communication optimize the operation of embodiments of the device by allowing any port of one transceiver to communicate with any port of the corresponding transceiver, thereby facilitating the increase of the data rate by multiple parallel communications. Both transceivers may have a another wired port, which is electrically coupled to transmit and receive data via a bus. The closed-loop waveguide and the couplers form a contactless rotary joint for bidirectional data transmission. In case of the CT gantry, data obtained by an X-Ray detector is transmitted via the rotatable transceiver through the contactless rotary joint to the stationary transceiver which is connected by bus to a stationary evaluation unit.

In at least one embodiment, the at least one rotatable transceiver has at least one RF port that separately optimizes transmission quality and/or data rate by controlling carrier frequency, phase, amplitude and modulation parameters of each port separately to establish a communication to any one or more RF ports of the stationary transceiver to separately match changing attenuation and phase during the rotation and to avoid crosstalk between the RF ports of the same transceiver.

Alternatively or in addition, and In a related embodiment, the at least one rotatable transceiver has two or more RF port that separately optimize transmission quality and/or data rate by controlling carrier frequency, phase, amplitude and modulation parameters of each port separately to any two or more RF ports of the stationary transceiver to separately match changing attenuation and phase during the rotation and to avoid crosstalk between the RF ports of the same transceiver and to establish multiple parallel communication channels during all times.

In yet another non-exclusive embodiment, a contactless datalink is configured to operate at an operating frequency within the EHF band. It may also be configured to operate at an operating frequency between 2.4 GHz and 30 GHz.

There are further embodiments having different combinations of waveguides, waveguide sections, transmitters and receivers. Examples of these embodiments are described in reference to the drawings in more detail.

BRIEF DESCRIPTION OF THE DRAWINGS

In the following, the invention will be described by way of example, without limitation of the general inventive concept, on examples of embodiment and with reference to the drawings.

Generally, the drawings are not to scale. Like elements and components are referred to by like labels and numerals. For the simplicity of illustrations, not all elements and components depicted and labeled in one drawing are necessarily labels in another drawing even if these elements and components appear in such other drawing.

While various modifications and alternative forms, of implementation of the idea of the invention are within the scope of the invention, specific embodiments thereof are shown by way of example in the drawings and are described below in detail. It should be understood, however, that the drawings and related detailed description are not intended to limit the implementation of the idea of the invention to the particular form disclosed in this application, but on the contrary, the intention is to cover all modifications, equivalents and alternatives falling within the spirit and scope of the present invention as defined by the appended claims.

DETAILED DESCRIPTION

Figure 1A:
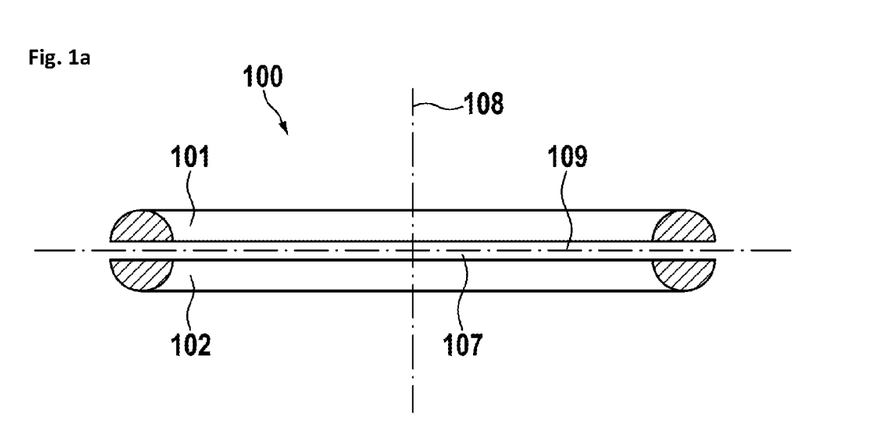
FIG. 1a, 1b, 1c present different modifications of an embodiment of a dielectric waveguide.

FIG. 1a illustrates a first embodiment of the waveguide structure, showing a portion of the dielectric waveguide 100. The dielectric waveguide 100 includes two waveguide components, preferably two identical and/or symmetrically-disposed components 101 and 102, forming a disc configuration. One component, for example, a first component 101 is mounted at the stationary part of the device, and a second component 102 is mounted at the rotatable part. The dielectric waveguide components may together (when considered combined) form a substantially round cross-section (as shown in FIG. 1a), or an oval or rectangular cross-section in the alternative. Notably, in an embodiment the rotatable and stationary parts to which the components 1-2. 102 are mounted may be exchanged. There is generally left a gap 107 between the two components along a plane 109 that may be orthogonal to the rotation axis 108.

Figure 1B:
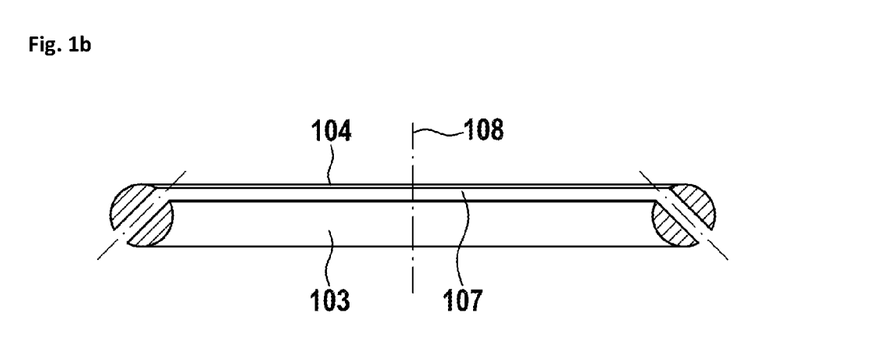
Figure 1C:
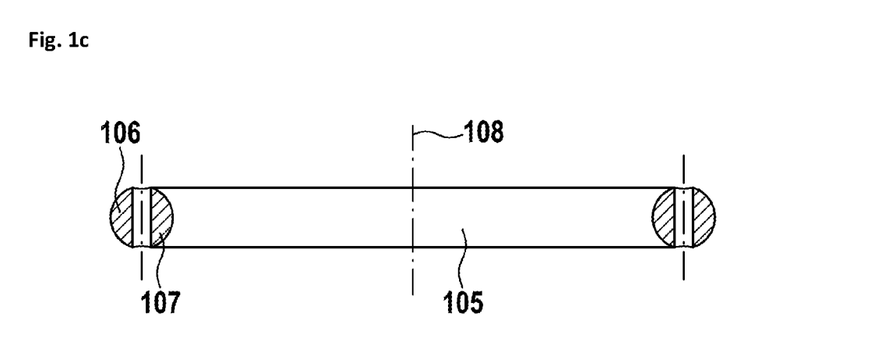

As shown in FIG. 1b, in a related embodiment of the waveguide structure, the ring waveguide including a first dielectric waveguide component 103 and a second dielectric waveguide component 104 may be formed such that the gap between these waveguide components 103, 104 is formed in a plane that, while being transverse to the rotation axis 108, is not exactly perpendicular to the axis 108 (as shown, the plane of the gap intersects the axis 108 at an angle, such as a slanted angle or a 45 degrees angle). In another embodiment, the ring including a first dielectric waveguide component 105 and a second dielectric waveguide component 106 may be split into two waveguide components 106, 107 (that is, formed by these two component) as shown in FIG. 1c along a cylindrical surface substantially parallel to the rotation axis to thereby form a drum configuration.

Any of the above-presented configurations allows for coupling of signals from either side to the other side.

Figure 2:
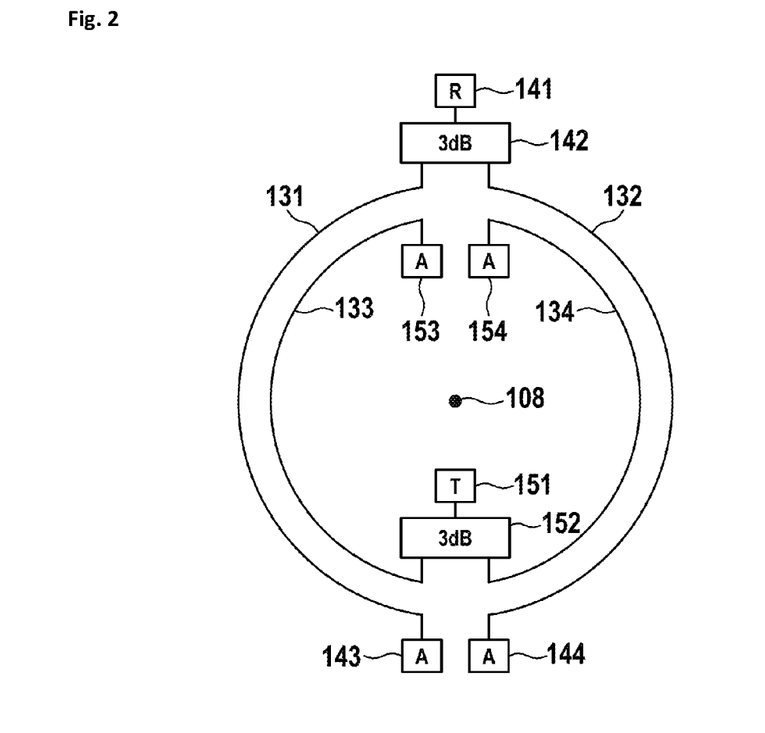
FIG. 2 presents a basic embodiment of a single channel unidirectional data communication.

In FIG. 2, a basic embodiment of the waveguide-containing portion of the device is shown, which may be based on a waveguide structure of the first embodiment of FIG. 1a. Here, a stationary waveguide (131, 132) including a first section 131 and a second section 132 is at a first part of the device. The rotatable waveguide of the device—the waveguide (133, 134)—also has a corresponding first section 133 and a corresponding second section 134. The stationary waveguide and the rotatable waveguide of the embodiment of FIG. 2 are in close contact with each other such that signals are easily coupled between the stationary and rotatable waveguides (131,132) and (133,134), preferably in both directions—from the stationary waveguide to the rotatable waveguide and from the rotatable waveguides to the stationary waveguides. Preferably, all waveguide sections 131, 132, 133, 134 have approximately the same lengths, and therefore cover about half the circumference of the corresponding rotational or stationary part, corresponding to an angular extent of approximately 180 degrees. The waveguide sections preferably have two ends. The first stationary waveguide section 131 and the second stationary waveguide section 132 are connected with their two ends that are close together (neighboring each other) to a 3 dB coupler 142, which is further coupled to a receiver 141. The coupler 142 is configured to combine, in operation, the signals from both stationary waveguide sections 121, 132 and forward these to the receiver 141. The opposing ends of the waveguide sections 131, 132 are coupled to absorbers 143 and 144. The rotatable waveguide sections 133 and 134 are connected with their ends that are close together to a 3 dB coupler 152, which is further connected to a transmitter 151. In operation, the signal from the transmitter 151 are forwarded to the 3 dB coupler 152, which splits such signal into two substantially equal signals that are then fed into each of the rotatable waveguide sections 133 and 134. The opposing ends of the rotatable waveguide sections are also terminated by absorbers 153 and 154.

Preferably, the transmitter 151 is configured to generate and modulate RF signals in the range of and above 60 GHz, and to couple a wave at such frequency(ies) into the dielectric waveguide, where the wave propagates towards the receiver 141.

Figure 3:
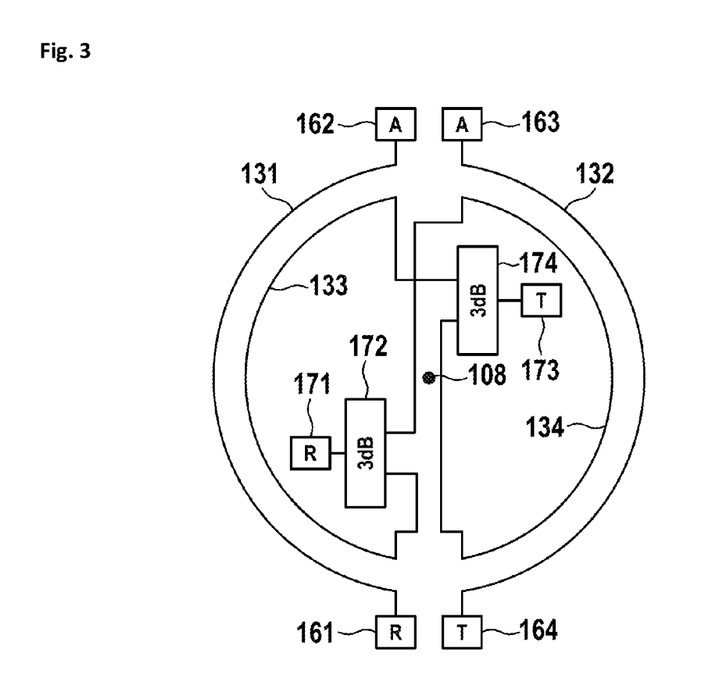
FIG. 3 illustrates a further embodiment of a single channel bidirectional data communication.

In FIG. 3, a related embodiment is schematically shown. Here, the curved stationary waveguide sections 131 and 132 are connected (at positions close to each other) with a transmitter 164 and a receiver 161, such that the first stationary waveguide section 131 is connected to the receiver 161, and the second stationary waveguide section 132 is connected to the transmitter 164. The first rotatable waveguide section 133, on the other hand, is connected at uts first end with a first 3 dB coupler 172, which is further connected to a receiver 171. The second end of the waveguide section 133 is connected to a second 3 dB coupler 174, which is further connected to a transmitter 173. Further, viewed in a clockwise direction, the first end of the second rotatable waveguide section 134 is connected to the first 3 dB coupler 172, whereas the second end of the second rotatable waveguide 134 is connected to the second 3 dB coupler 174. This criss-cross connection allows for a signal transmission without change in phase. The angular gap between the ends of line prevents cross-coupling between the ends of the rotatable waveguide sections 133 and 134.

Figure 4:
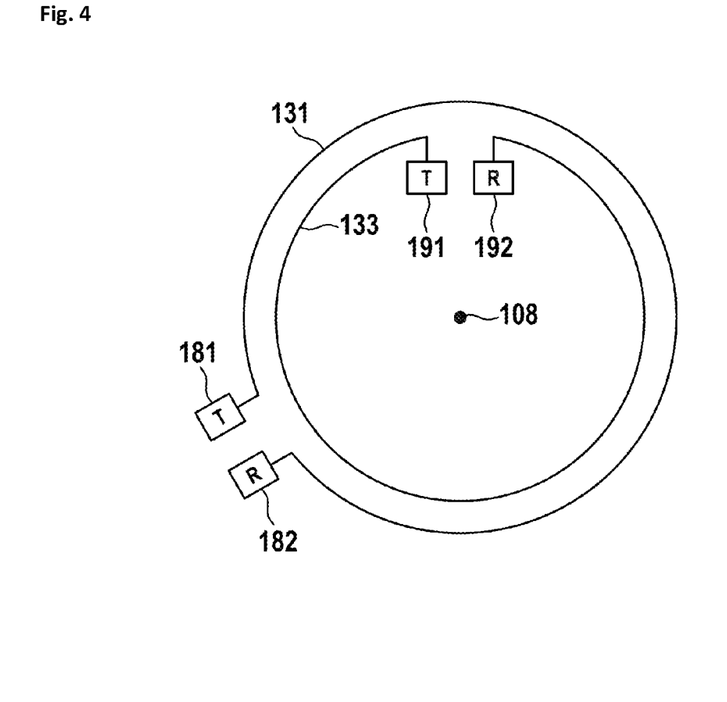
FIG. 4 shows a related embodiment of a multichannel bidirectional data communication.

In FIG. 4, yet another related embodiment is shown with only one first waveguide 131 and one second waveguide 133. The first waveguide 131 is connected at one end to a receiver 182 and at the opposing end to a transmitter 181. The second waveguide 133 is connected at a first to a receiver 192 and at the opposing end to a transmitter 191. The link is structured such that transmitter and receiver are arranged opposite to one another as far as the directions of propagations of the signals is concerned. A spatial gap between receiver and transmitter causes a high signal attenuation between receiver and transmitter.

Alternatively, and in a related embodiment, to arrive at a configuration somewhat similar to that of FIG. 4, the ends of the two stationary waveguide sections (each covering approximately half of the circumference of the stationary part of the device) can be joined to a single waveguide 131, the free ends of which are then connected to the transceiver combining receiver 182 and transmitter 181, respectively. At the same time, the ends of the two rotatable waveguide sections (each covering approximately half of the circumference of the rotatable part o the device) can be joined to a single waveguide 133, the free ends of which are then connected to the transceiver combining receiver 192 and transmitter 191.

Figure 5:
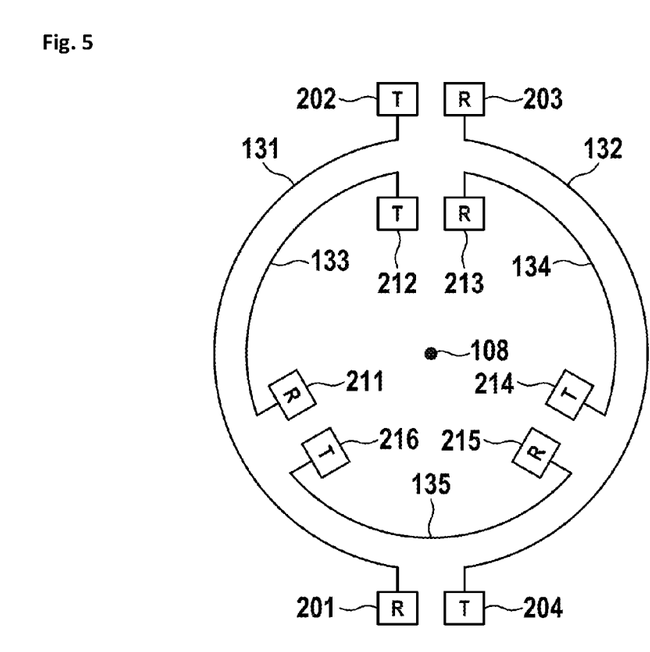
FIG. 5 presents a further embodiment of a multichannel bidirectional data communication.

In FIG. 5, a further embodiment is shown, where the stationary waveguide includes a first stationary waveguide section 131 and a second stationary waveguide section 132 (which have substantially the same lengths and therefore have an angular extend of about 180 degrees each). The rotatable waveguide includes a first rotatable waveguide section 133, a second rotatable waveguide section 134, and a third rotatable waveguide section 135 (which all have about the same size, and therefore cover corresponding angles of about 120 degrees). The first stationary waveguide section 131 is connected at a first end to a receiver 201 and to a transmitter 202 at the opposing end. As viewed clockwise next to this end, the first end of the second stationary waveguide section 132 is connected to a receiver 203, and the opposing end to a transmitter 204. Therefore, transmitters and receivers present in this embodiment are alternatingly connected at the ends of the sections of the first stationary waveguide, such that a receiver is followed by a transmitter in a clockwise view. At the rotatable waveguide sections 133, 134, 15, there is basically the same arrangement, such that a transmitter is followed by a receiver in a clockwise view on each of the three sections. Therefore, the first rotatable waveguide section 133 has a receiver 211 at a first end thereof and opposing thereto a transmitter 212. Next to it, the second rotatable waveguide section 134 has a receiver 213 at its first end and a transmitter 214 at its second end. This is followed by the third rotatable waveguide section having a receiver 215 at its first end and a transmitter 216 at its second end. The second end of the third rotatable waveguide section 135 with the transmitter 216 is disposed close to the first end of the first rotatable waveguide section 133 with the receiver 211. In a related embodiment, the sequence of transmitters and receivers may be reversed.

Also, one end of the first stationary waveguide section 131 and 132 can be joined together to form a single (loop) waveguide connected, on one hand, to a transceiver device that combines the receiver 203 and the transmitter 202, on the other hand, to another transceiver device combining the receiver 201 and the transmitter 204. Also, receiver 213 and transmitter 212, receiver 215 and transmitter 214 and receiver 211 and transmitter 216 can be paired to transceivers.

Figure 6:
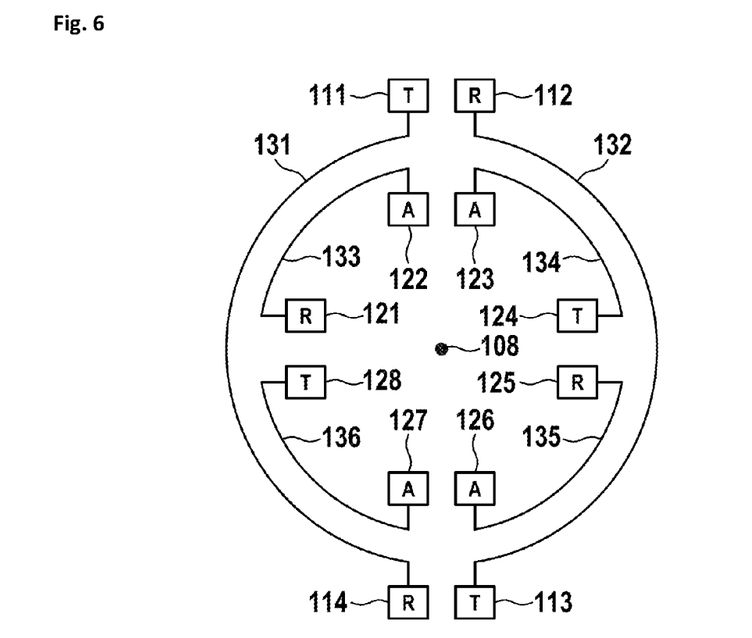
FIG. 6 depicts a further embodiment.

In FIG. 6, a further embodiment is shown. A first part, for example the stationary part, may bear stationary waveguide sections 131, 132. A second part, for example a rotatable part, may bear rotating waveguide sections 133, 134, 135, 136 which all have about the same size, and therefore cover angles of about 90 degrees each. The stationary waveguides 131, 132 have receivers 112, 114 at their first ends and transmitters 111, 113 at their second ends. Accordingly, in the clockwise direction, first waveguide 131 has a receiver 114 at its first end and a transmitter 111 at its second end, whereas the first waveguide 132 has a receiver 112 at its first end and a transmitter 113 at its second end.

Each of the rotatable waveguides have either a transmitter or a receiver at one end, and an absorber at the opposing end. Here, the first rotatable waveguide 133 is show to have, as viewed in a clockwise direction, at its first end a receiver 121 and an absorber 122 opposing thereto. The second rotatable waveguide section 134 has an absorber 123 at an end close to the absorber 122 and a transmitter 124 opposing thereto. The third rotatable waveguide section 135 has a receiver 125 close to the transmitter 124 and opposing thereto an absorber 126. The fourth rotatable waveguide section 136 has an absorber 127 close to the absorber 1226 and opposing thereto a transmitter 128.

The function and, therefore, positioning of the rotatable and the stationary parts may be exchanged. Furthermore, the orientation of the transmitters or receivers may be exchanged with respect to the waveguides. In any case, in each of the embodiments, each of the transmitters may be exchanged by a receiver, and each of the receivers may be exchanged by a transmitter.

All transmitters and receivers shown in FIGS. 4, 5, and 6 as well as receiver 161 and transmitter 164 in FIG. 3 may be combined to a transceiver when both half waveguides are combined to a full waveguide in direct vicinity of the transceivers.

Figure 7:
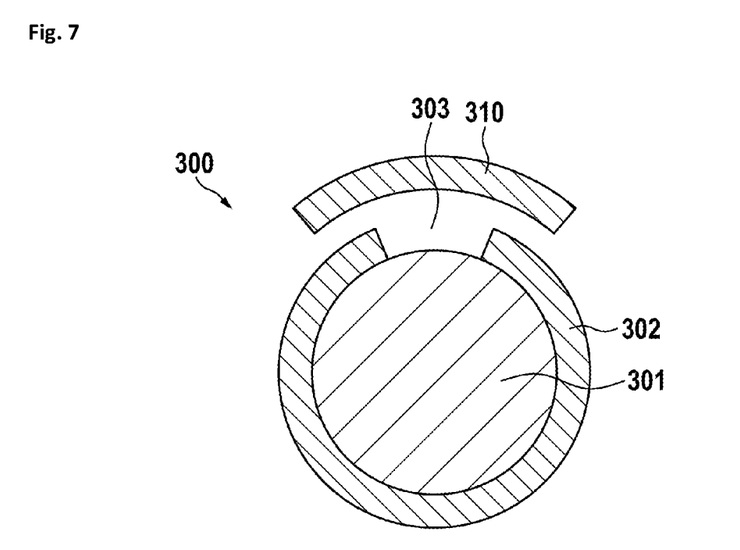
FIG. 7 presents a basic concept of a further dielectric waveguide in a sectional view.

In FIG. 7, a basic concept of a further dielectric waveguide embodiment 300 is shown in a sectional view. The waveguide has a dielectric core 301 and a metallic shield 302, which has a gap 303. For coupling a signal, there may be a pickup 310 that preferably has only a short length of few millimeters or few centimeters (as compared to the total length of the dielectric waveguide, which may be in the range of several meters). The embodiment is configured to ensure that energy may only be radiated out of the gap at a position where the pickup is located, as there the impedance should be matched.

Figure 8:
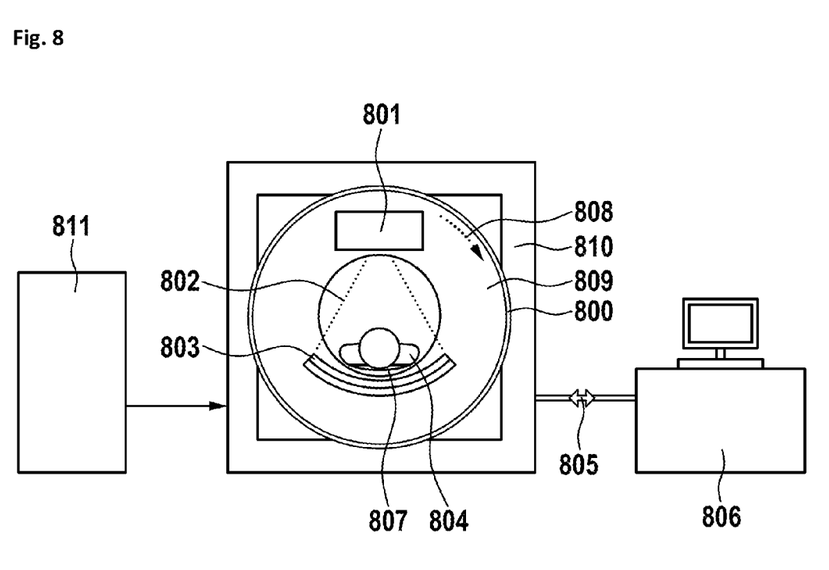
FIG. 8 presents schematically a CT (Computed Tomography) scanner gantry.

FIG. 8 shows schematically a CT (Computed Tomography) scanner gantry. The stationary part is suspended within and is part of a massive frame 810. The rotatable part 809 of the gantry is rotatably mounted with respect to the stationary part and rotates along the rotation direction 808. It supports an X-ray tube 801 for generating an X-ray beam 802 that radiates through a patient 804 lying on a table 807 and which is intercepted by a detector 803 and converted to electrical signals and imaging data thereof. Electrical power from power supply unit 811 may be transmitted by a slipring (not shown) to the rotatable part. The data obtained by the detector 803 are transmitted via contactless rotary joint 800 to an evaluation unit 806 by means of a data bus or network 805.

In the following description of FIGS. 9, 10, 11, the closed-loop dielectric waveguide 400 is considered, but referred to as "waveguide 400" of "waveguide structure 400", for simplicity of presentation.

Figure 9:
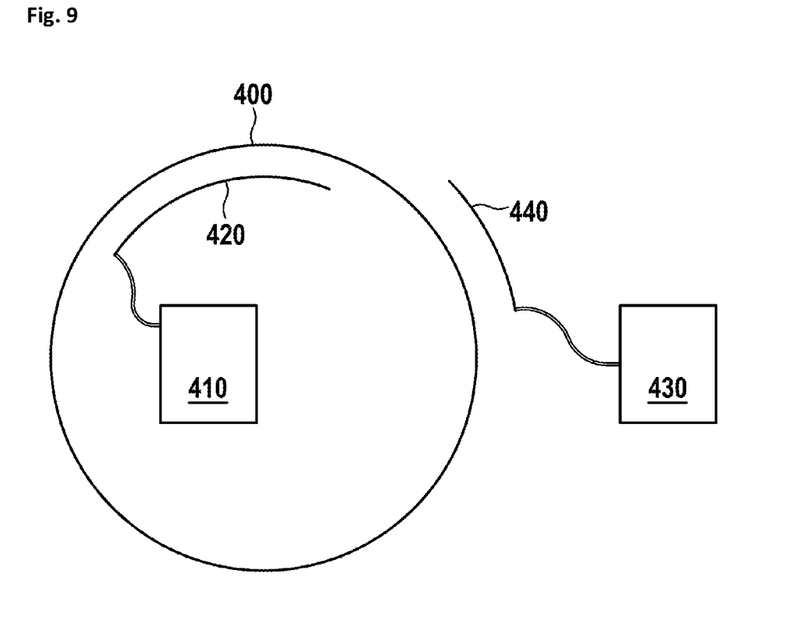
FIG. 9 presents a further bidirectional embodiment employing transceivers.

In FIG. 9, an embodiment is shown which may be based on a standard dielectric waveguide structure 400 that is dimensioned to form a closed loop and that includes one part that is conformed to a circle (where either both ends of the waveguide are glued or welded together or where such waveguide is initially configured as a circular loop, as one part). This circular dielectric waveguide might be fixed to the stator (stationary part) or fixed to the rotor (rotatable part). The cross-section of the waveguide 400 might be shaped circularly, elliptically, as an oval, or rectangularly, or\have any other shape suited to guide a target wave.

Also, this waveguide 400 might be substantially identical to one waveguide section 101 as described in FIG. 1, that means it is only one section of a dielectric waveguide split into two sections where either section can guide a wave but also the combined sections.

Two couplers (420, 440) formed of a standard dielectric waveguide as described may be used to couple a wave in and/or out of the waveguide 400. These couplers are kept in close distance preferably in the range of $1/6^{th}$ to $1/10^{th}$ of a wavelength in air, the distance may vary because of mechanical tolerances between near zero and up to $1/4^{th}$ of a wavelength. The couplers preferably are mounted as circular segments having the same center point as the waveguide 400. The lengths of each of the two couplers preferably are substantially identical and are shorter than half of the total circumference.

The waveguide 400 might also be configured to rotate at a different speed than that of the rotatable coupler. Since in an embodiment, the waveguide 400 is configured as either rotatable or stationary waveguide, one of the couplers might be mounted in a fixed position and distance to the waveguide 400. The rotatable coupler 440 is mounted in such a way that it cannot collide with the stationary coupler during rotation. This means that one coupler (e.g. the stationary coupler 420 as in this figure) can be mounted on the inner side of the waveguide 400, the other coupler (e.g. the rotatable coupler 440 as in this Figure) on the outer diameter. Alternatively, the couplers can be mounted before or behind the waveguide 400 or at any angular disposition where a collision is avoided.

One or both of the couplers 420, 440 can also be part of a waveguide section 102 as described in FIG. 1, that means that the coupler is formed of a part of the other section of a waveguide split into two sections where either section can guide a wave but also the combined sections. Preferably this is the rotatable coupler 440 when the waveguide 400 is stationary.

The transceivers 410, 430 include a transmitter and receiver that are connected to one port of the transceiver for wireless transmission and reception of. This port can also be used for "wired" communication through a dielectric waveguide if the port is coupled to a dielectric waveguide capable to guide the wave. The stationary transceiver 410 having one port to transmit and receive signals wireless and is connected to the stationary coupler 420 either by a connecting dielectric waveguide or by directly coupling a wave into the coupler e.g. by an antennaor by a coaxial cable connecting the transceiver to an antenna which then couples the signal into the coupler. The stationary transceiver 410 has one port to transmit and receive signals wirelessly and is connected to the stationary coupler 420. (Similarly, the rotatable transceiver 430 has one port to transmit and receive signals wirelessly and is connect to the rotatable coupler 440.) The waveguide 400 and couplers 420, 440 that are also formed of waveguides as described, are in close contact with each other such that signals are operably coupled between the stationary and rotatable couplers with the waveguide 400 in between, preferably in both directions.

In the configuration described in this FIG. 9 data transmitted up (from stationary transceiver 410 to rotary transceiver 430) are propagating as waves in the waveguide 400 in clockwise direction, the data transmitted down (from rotary transceiver 430 to stationary transceiver 410) are propagating in the counter-clockwise direction. Preferably the waveguide 400 has an attenuation low enough to allow communication between the both transceivers during a first round of the waves travelling but high enough not to distort the receiver after the first round is completed Preferably, the stationary transceiver 410 generates and modulates RF signals in the range of and above 60 GHz and couples a wave into the dielectric waveguide where it propagates towards the rotary transceiver 430 and vice versa. The technology can also be used with all carrier frequencies that can be coupled into dielectric waveguides, e.g. operating at 2.4 GHz or 5 GHz or any frequency above that but below optical frequencies.

Both transceivers have a another wired port that is not shown which is electrically coupled to transmit and receive data via a bus. The waveguide 400 and the couplers 410, 430 form a contactless rotary joint for bidirectional data transmission. In case of the CT gantry shown and described in FIG. 8. The data obtained by the detector 803 of FIG. 8 is transmitted via the rotatable transceiver 430 through the contactless rotary joint described in FIG. 9 to the stationary transceiver which is connected by bus (not shown) to the stationary evaluation unit 806 of FIG. 8 where the data are received, control data are transmitted in the opposite direction.

Figure 10:
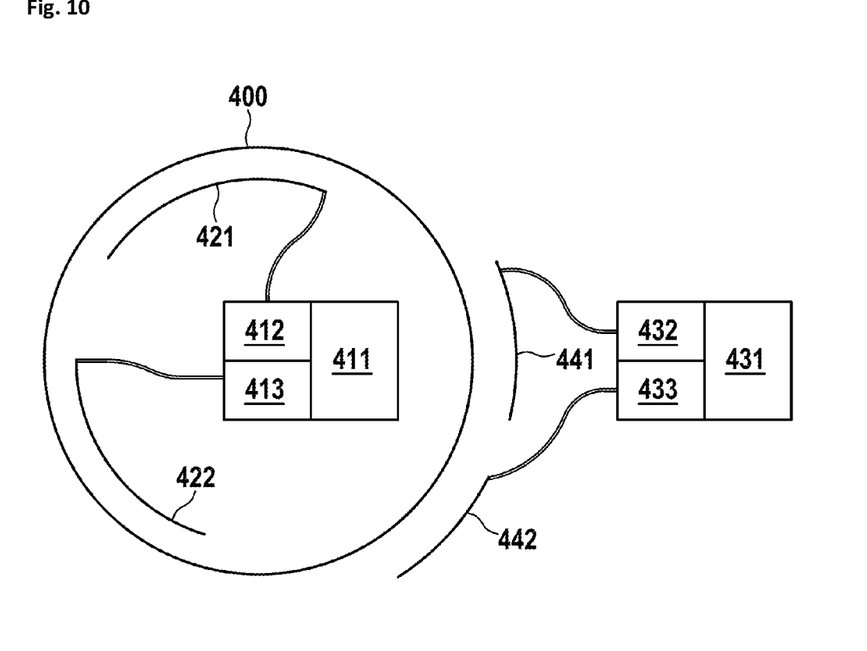
FIG. 10 illustrates a further bidirectional embodiment employing transceivers.
Figure 11:
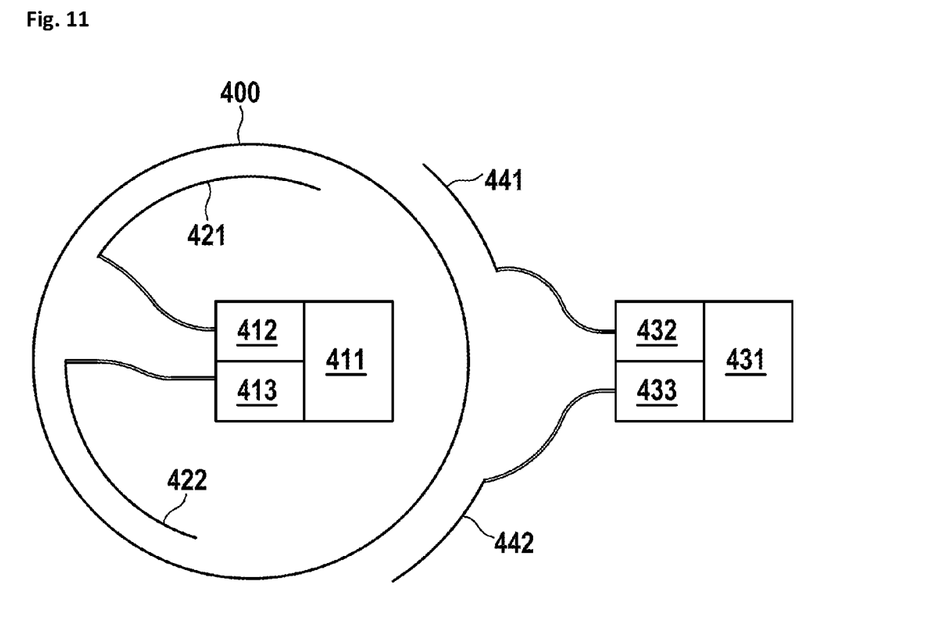
FIG. 11 presents a further bidirectional embodiment employing transceivers.

FIG. 10 illustrates the same principle setup of rotatable couplers and waveguide 400 as in FIG. 9. The difference between the embodiments of FIG. 10 and FIG. 9 is that in FIG. 10 a multiport transceiver 411 with at least a first stationary port 412 and at least a second stationary port 413 is configured to optimize transmission quality and/or data rate by controlling carrier frequency, phase, amplitude and modulation parameters of each of these RF porst to separately match changing attenuation and phase during the rotation and to avoid crosstalk between the channels of the transceiver 411; and a multiport transceiver 431 with at least a first rotatable port 432 and at least a second rotatable port 433 is configured to optimize transmission quality and/or data rate by controlling carrier frequency, phase, amplitude and modulation parameters of each of these RF ports to separately match changing attenuation and phase during the rotation and to avoid crosstalk between the channels of the transceiver 431.

In the configuration described data transmitted up (from stationary multiport transceiver 411 to rotary/rotatable multiport transceiver 431) are propagating as modulated waves in the waveguide in clockwise direction, the data transmitted down (from rotary multiport transceiver 431 to stationary transceiver 411) are propagating in the contrary direction. Preferably the waveguide 400 has an attenuation low enough to allow communication between the both transceivers during a first half round of the waves travelling but high enough not to distort the receiver after the first round is completed In this configuration, the first stationary port 412 and the second stationary port 413 of the stationary multiport transceiver 411 communicate via first stationary coupler 421, second stationary coupler 422, waveguide 400 and first rotatable coupler 441, second rotatable coupler 442 with the first rotatable port 432 and the second rotatable port 433 of the rotatable multiport transceiver 431. The transceivers select as inputs the RF port with the best communication quality, which changes during rotation, typically determined by bit error rate. To optimize the transmission by lowering the crosstalk between the channels the first and second rotatable couplers 441,442 may be positioned approximately 180 degrees apart of each other. The same applies for the first and second rotatable couplers 441,442 which preferably are positioned approximately 180 degrees apart of each other. With n (n=1, 2, 3, 4, 5, . . . ) ports the displacement of the couplers should be approximately 360 degrees divided by n. FIG. 10 shows a displacement of approximately 90 degrees. Here, the stationary waveguide couplers 421, 422 are shown connected to the stationary transceiver 411 and the ends of these two couplers that are separated from one another at least by a length of one of these two couplers. Similarly the rotatable waveguide couplers 441, 442 are shown connected to the rotatable transceiver 431 at the ends of these two couplers that are separated from one another at least by a length of one of these two couplers.

Preferably the transceivers are employing the MIMO (multiple in-multiple out) technology as e.g. defined in recent substandards of IEEE-802.11-(WiFi/WLAN-Standard) e.g. IEEE-802.11n and newer substandards-(WiFi/WLAN-Standard). Another implementation into a widely used commercial standard is LTE at e.g. 2.6 GHz. These standards for wireless communication optimize by allowing any port of one transceiver to communicate with any port of the corresponding transceiver. FIG. 11 is similar to FIG. 10.

In the configuration port the first stationary port 412 of the stationary multiport transceiver 411 communicates via stationary coupler 421, waveguide 400 and rotatable coupler 441 with port the first rotatable port 432 of the rotatable multiport transceiver 431, the second stationary port 413 of the stationary multiport transceiver 411 communicates via stationary coupler 421, waveguide 400 and rotatable coupler 441 with the second rotatable port 433 of the rotatable multiport transceiver 431.

Here preferably the closed loop waveguide 400 has an attenuation low enough to allow communication between the both transceivers during a first half round of the waves travelling but high enough not to distort the receiver after the first round is completed. To optimize the transmission the first and second rotatable couplers 441, 442 may be positioned approximately 180 degrees apart of each other. The same applies for the first and second rotatable couplers 441, 442 which may be positioned approximately 180 degrees apart of each other. With n (n=1, 2, 3, 4, 5, . . . ) ports the displacement of the couplers should be approximately 360 degrees divided by n. FIG. 11 shows a displacement of approximately 90 degrees. Here, the stationary waveguide couplers 421, 422 are shown connected to the stationary transceiver 411 and the ends of these two couplers that are located close to one another. Similarly the rotatable waveguide couplers 441, 442 are shown connected to the rotatable transceiver 431 at the ends of these two couplers that are located close to one another.

It will be appreciated to those skilled in the art having the benefit of this disclosure that this invention is believed to provide contactless datalinks between rotatable parts. Further modifications and alternative embodiments of various aspects of the invention will be apparent to those skilled in the art in view of this description. Accordingly, this description is to be construed as illustrative only and is provided for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

LIST OF REFERENCE NUMERALS 100 ring shaped dielectric waveguide
101 first dielectric waveguide component
102 second dielectric waveguide component
103 first dielectric waveguide component
104 second dielectric waveguide component
105 first dielectric waveguide component
106 second dielectric waveguide component
107 gap
108 rotation axis
109 plane
111 transmitter
112 receivers
113 transmitter
114 receivers
121 receiver
122 absorber
123 absorber
124 transmitter
125 receiver
126 absorber
127 absorber
128 transmitter
131 first stationary waveguide section
132 second stationary waveguide section
133 first rotatable waveguide section
134 second rotatable waveguide section
135 third rotatable waveguide section
136 fourth rotatable waveguide section
141 receiver
142 3 dB coupler
143 absorber
144 absorber
151 transmitter
152 3 dB coupler
153 absorber
154 absorber
161 transmitter
164 receiver
171 receiver
172 first 3 dB coupler
173 transmitter
174 second 3 dB coupler
181 transmitter
182 receiver
191 transmitter
192 receiver
201 receiver
202 transmitter
203 receiver
204 transmitter
211 receiver
212 transmitter
213 receiver
214 transmitter
215 receiver
216 transmitter
300 dielectric waveguide
301 dielectric core
302 metallic shield
303 gap
310 pickup
400 closed loop dielectric waveguide
410 stationary transceiver
411 stationary multiport transceiver
412 first stationary port
413 second stationary port
420 stationary coupler
421 first stationary coupler
422 second stationary coupler
430 rotatable transceiver
431 rotatable multiport transceiver
432 first rotatable port
433 second rotatable port
440 rotatable coupler
441 first rotatable coupler
442 second rotatable coupler
800 contactless rotary joint
801 x-ray tube
802 x-ray beam
803 x-ray detector
804 patient
805 network
806 evaluation unit
807 patient table
808 rotation direction
809 rotatable part
810 frame
811 power supply unit

The invention claimed is:

1. A contactless datalink configured to transmit data between a stationary part and a rotatable part and configured to rotate around an axis of rotation, the datalink comprising a ring-shaped dielectric waveguide,
   wherein:
   (a) the ring-shaped dielectric waveguide includes a first dielectric waveguide component at the rotatable part and a second dielectric waveguide component at the stationary part;
   (b) the ring-shaped dielectric waveguide has a center axis aligned with the axis of rotation;
   (c) the ring-shaped dielectric waveguide has a gap between the first dielectric waveguide component and the second dielectric waveguide component;

(d) the first dielectric waveguide component includes a first rotatable waveguide section and a second rotatable waveguide section, each of the first and second rotatable waveguide sections having two corresponding rotatable waveguide section ends,
wherein a first end of the two corresponding rotatable waveguide section ends is connected to at least one of a first transmitter, a first receiver, and a first absorber and a second end of the two rotatable waveguide section ends is connected to at least one of a second transmitter, a second receiver, and a second absorber,
wherein corresponding first ends of the first and second rotatable sections are disposed close together and corresponding second ends of the first and second rotatable sections are disposed close together;
(e) the second dielectric waveguide component includes a first stationary waveguide section and a second stationary waveguide section, each of the first and secondary waveguides sections having two corresponding stationary waveguide section ends,
wherein a first end of the two corresponding stationary waveguide sections ends is connected to at least one of a third transmitter, a third receiver, and a third absorber and a second end of the two stationary waveguide sections ends is connected to at least one of a fourth transmitter, a fourth receiver, and a fourth absorber,
wherein corresponding first ends of the first and second stationary sections are disposed close together and corresponding second ends of the first and second stationary sections are disposed close together;
(f) the first end of the first stationary waveguide section is connected to a receiver of the third and fourth receivers and the first end of the second stationary waveguide section is connected to a transmitter of the third and fourth transmitters;
(g) the second ends of the first and second stationary sections are terminated by the third and fourth absorbers, respectively,
(h) the first end of the first rotatable waveguide section and the second end of the second rotatable waveguide section are connected by a first 3 dB coupler to a transmitter of the first and second transmitters; and
(i) the second end of the first rotatable waveguide section and the first end of the second rotatable waveguide section are connected by a second 3 dB coupler to a receiver of the first and second receivers.

2. The contactless datalink of claim 1, wherein the first dielectric waveguide component has a structure identical to a structure of the second dielectric waveguide component.

3. The contactless datalink of claim 1, wherein at least one of the following conditions is satisfied:
the first and second rotatable waveguides sections have equal lengths,
and
the first and second stationary waveguide sections have having equal lengths.

4. A contactless datalink configured to transmit data between a stationary part and a rotatable part and configured to rotate around an axis of rotation, the datalink comprising a ring-shaped dielectric waveguide,
wherein:

(a) the ring-shaped dielectric waveguide includes a first dielectric waveguide component at the rotatable part and a second dielectric waveguide component at the stationary part;
(b) the ring-shaped dielectric waveguide includes a center axis aligned with the axis of rotation;
(c) the ring-shaped dielectric waveguide includes a gap between the first dielectric waveguide component and the second dielectric waveguide component;
(d) the first dielectric waveguide component includes at least one rotatable waveguide section, the at least one t rotatable waveguide section having two rotatable waveguide section ends,
wherein one end of said two rotatable waveguide section ends is connected to at least one of a first transmitter, a first receiver, and a first absorber and the other end of said two rotatable waveguide section ends is connected to at least one of a second transmitter, a second receiver, and a second absorber;
(e) the second dielectric waveguide component includes at least one stationary waveguide section, the at least one stationary waveguide section having two stationary waveguide section ends,
wherein one end of said two stationary section ends is connected to at least one of a third transmitter, a third receiver, and a third absorber and the other end of said two stationary section ends is connected to at least one of a fourth transmitter, a fourth receiver, and a fourth absorber;
wherein one end of said at least one rotatable waveguide section is connected to a transmitter of the first and second transmitters and the other end of said at least one rotatable waveguide section is connected to a receiver of the first and second receivers; and
wherein one end of said stationary waveguide section is connected to a transmitter of the third and fourth transmitters, and the other end of said stationary waveguide section is connected to a receiver of the third and fourth receivers.

5. The contactless datalink of claim 4, wherein the first dielectric waveguide component has a structure identical to a structure of the second dielectric waveguide component.

6. The contactless datalink of claim 4, wherein at least one of the following conditions is satisfied:
the at least one rotatable waveguide section includes multiple rotatable waveguide section having equal lengths,
and
the at least one stationary waveguide section includes multiple stationary waveguide section having equal lengths.

7. A contactless datalink configured to transmit data between a stationary part and a rotatable part and configured to rotate around an axis of rotation, the datalink comprising a ring-shaped dielectric waveguide,
wherein:
(a) the ring-shaped dielectric waveguide includes a first dielectric waveguide component at the rotatable part and a second dielectric waveguide component at the stationary part;
(b) the ring-shaped dielectric waveguide includes a center axis aligned with the axis of rotation;
(c) the ring-shaped dielectric waveguide includes a gap between the first dielectric waveguide component and the second dielectric waveguide component;

(d) the first dielectric waveguide component includes at least one rotatable waveguide section, the at least one t rotatable waveguide section having two rotatable waveguide section ends, wherein one end of said two rotatable waveguide section ends is connected to at least one of a first transmitter, a first receiver, and a first absorber and the other end of said two rotatable waveguide section ends is connected to at least one of a second transmitter, a second receiver, and a second absorber;

(e) the second dielectric waveguide component includes at least one stationary waveguide section, the at least one stationary waveguide section having two stationary waveguide section ends, wherein one end of said two stationary section ends is connected to at least one of a third transmitter, a third receiver, and a third absorber and the other end of said two stationary section ends is connected to at least one of a fourth transmitter, a fourth receiver, and a fourth absorber;

wherein the at least one rotatable waveguide section is coupled to a transmitter of the first and second transmitters, and the at least one stationary waveguide section is coupled to a receiver of the third and fourth receivers;

and wherein a width of the gap between the first and second dielectric waveguide components is in a range from $1/10$th to $1/6$th of a wavelength of a signal wave to be transmitted in air.

8. The contactless datalink of claim 7, wherein the first dielectric waveguide component has a structure identical to a structure of the second dielectric waveguide component.

9. The contactless datalink of claim 7, wherein at least one of the following conditions is satisfied:

the at least one rotatable waveguide section includes multiple rotatable waveguide section having equal lengths and the at least one stationary waveguide section includes multiple stationary waveguide section having equal lengths.

10. A contactless datalink configured to transmit data between a rotatable part and a stationary part, the datalink comprising:

a closed-loop dielectric waveguide, at least one stationary coupler, at least one rotatable coupler, at least one stationary transceiver coupled to the at least one stationary coupler, and at least one rotatable transceiver coupled to the at least one rotatable coupler, wherein said contactless datalink is configured to operate at an operating frequency within the EHF band or at an operating frequency between 2.4 GHz and 30 GHz.

11. The contactless datalink of claim 10, wherein the at least one stationary coupler includes a pair of stationary waveguide couplers, the at least one rotatable coupler includes a pair of rotatable waveguide couplers, and wherein one of the following conditions is satisfied:

a) first and second couplers of each of the pair of stationary waveguide couplers and the pair of rotatable waveguide couplers are connected to a respectively-corresponding transceiver, of the at least one stationary transceiver and the at least one rotatable transceiver, at first ends of said first and second couplers said first ends being disposed close to one another; and b) said first and second couplers are connected to the respectively-corresponding transceiver at second ends of said first and second couplers, said second end being separated from one another by at least a length of a coupler of the first and second couplers.

12. The contactless datalink of claim 10, wherein the at least one rotatable transceiver has at least two RF ports, and the at least one stationary transceiver has at least two RF ports, wherein said contactless datalink includes multiple closed-loop waveguides that are configured to transmit data in parallel, and wherein the at least one stationary transceiver that is coupled to the at least one stationary coupler and at the least one rotatable transceiver that is coupled to the at least one rotatable coupler are connected to a corresponding of said multiple closed-loop waveguides.

13. The contactless datalink of claim 10, wherein the at least one rotatable transceiver has at least one RF port configured to separately optimize at least one of transmission quality and data rate by controlling carrier frequency, phase, amplitude, and modulation parameters to establish a communication with at least one RF port of the at least one stationary transceiver to separately match changing attenuation and phase during rotation and to avoid crosstalk between corresponding RF ports of either of the at least one rotatable transceiver and the at least one stationary transceiver.

14. The contactless datalink of claim 10, wherein the at least one rotatable transceiver has two or more RF ports configured to separately optimize at least one of transmission quality and data rate by controlling carrier frequency, phase, amplitude and modulation parameters to establish a communication with any two or more RF ports of the at least one stationary transceiver to separately match changing attenuation and phase during the rotation and to avoid crosstalk between the RF ports of either of the at least one rotatable transceiver and the at least one stationary transceiver and to establish multiple parallel communication channels during all times.

\* \* \* \* \*